(12) United States Patent
Strobl et al.

(10) Patent No.: US 9,168,090 B2
(45) Date of Patent: Oct. 27, 2015

(54) ELECTROSURGICAL INSTRUMENT WITH RESTRICTED TRIGGER

(71) Applicant: Ethicon Endo-Surgery, Inc., Cincinnati, OH (US)

(72) Inventors: Geoffrey S. Strobl, Williamsburg, OH (US); David A. Witt, Maineville, OH (US); Zhifan F. Huang, Mason, OH (US); Mary E. Mootoo, Cincinnati, OH (US); Timothy G. Dietz, Wayne, PA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 94 days.

(21) Appl. No.: 13/826,108

(22) Filed: Mar. 14, 2013

(65) Prior Publication Data
US 2014/0276732 A1 Sep. 18, 2014

(51) Int. Cl.
*A61B 18/14* (2006.01)
*A61B 18/00* (2006.01)
*A61B 17/32* (2006.01)

(52) U.S. Cl.
CPC ..... *A61B 18/1445* (2013.01); *A61B 17/320068* (2013.01); *A61B 2018/00196* (2013.01); *A61B 2018/00708* (2013.01); *A61B 2018/00958* (2013.01); *A61B 2018/1455* (2013.01)

(58) Field of Classification Search
USPC .................................................. 606/51, 205
See application file for complete search history.

(56) References Cited

U.S. PATENT DOCUMENTS

| | | | |
|---|---|---|---|
| 4,805,823 | A | 2/1989 | Rothfuss |
| 5,415,334 | A | 5/1995 | Williamson, IV et al. |
| 5,465,895 | A | 11/1995 | Knodel et al. |
| 5,597,107 | A | 1/1997 | Knodel et al. |
| 5,632,432 | A | 5/1997 | Schulze et al. |
| 5,673,840 | A | 10/1997 | Schulze et al. |
| 5,704,534 | A | 1/1998 | Huitema et al. |
| 5,814,055 | A | 9/1998 | Knodel et al. |
| 6,500,176 | B1 | 12/2002 | Truckai et al. |
| 6,783,524 | B2 | 8/2004 | Anderson et al. |
| 6,978,921 | B2 | 12/2005 | Shelton, IV et al. |
| 7,000,818 | B2 | 2/2006 | Shelton, IV et al. |
| 7,112,201 | B2 | 9/2006 | Truckai et al. |
| 7,125,409 | B2 | 10/2006 | Truckai et al. |
| 7,143,923 | B2 | 12/2006 | Shelton, IV et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,303,108 | B2 | 12/2007 | Shelton, IV et al. |
| 7,309,849 | B2 | 12/2007 | Truckai et al. |
| 7,311,709 | B2 | 12/2007 | Truckai et al. |

(Continued)

OTHER PUBLICATIONS

U.S. Appl. No. 61/410,603, filed Nov. 5, 2010.

(Continued)

*Primary Examiner* — Nicole F Lavert
(74) *Attorney, Agent, or Firm* — Frost Brown Todd LLC

(57) ABSTRACT

An apparatus for operating on tissue includes an end effector, a first actuator, and a second actuator. The end effector includes a first jaw pivotable relative to a second jaw to a closed position. The first actuator is movable from a first position to a second position to pivot the first jaw to the closed position. The first actuator engages the second actuator in the second position to selectively provide RF energy to the end effector.

20 Claims, 14 Drawing Sheets

(56) References Cited

U.S. PATENT DOCUMENTS

| | | |
|---|---|---|
| 7,354,440 B2 | 4/2008 | Truckal et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,434,715 B2 | 10/2008 | Shelton, IV et al. |
| 7,628,791 B2 | 12/2009 | Garrison et al. |
| 7,721,930 B2 | 5/2010 | McKenna et al. |
| 8,408,439 B2 | 4/2013 | Huang et al. |
| 8,453,914 B2 | 6/2013 | Laurent et al. |
| 8,461,744 B2 | 6/2013 | Wiener et al. |
| 8,764,747 B2 | 7/2014 | Cummings et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0137337 A1* | 6/2011 | van den Dool et al. ....... 606/205 |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0116379 A1 | 5/2012 | Yates et al. |
| 2013/0023868 A1 | 1/2013 | Worrell et al. |
| 2013/0030428 A1 | 1/2013 | Worrell et al. |
| 2013/0053831 A1 | 2/2013 | Johnson et al. |

OTHER PUBLICATIONS

International Search Report dated Jun. 6, 2014 for Application No. PCT/US2014/017119.

U.S. Appl. No. 61/550,768, filed Oct. 24, 2011.

International Written Opinion dated Jun. 6, 2014 for Application No. PCT/US2014/017119.

* cited by examiner

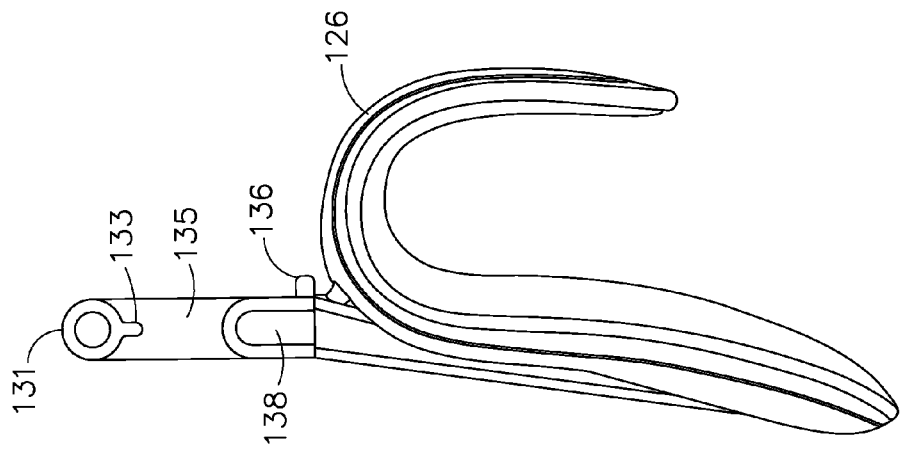
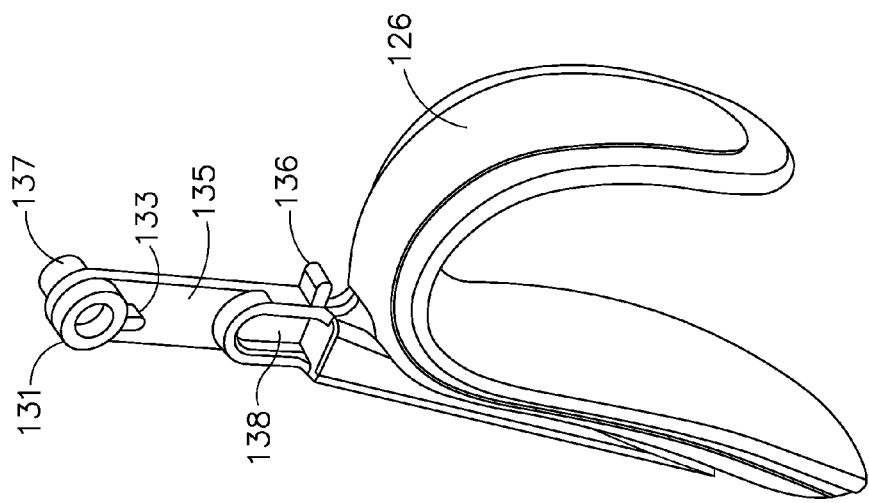

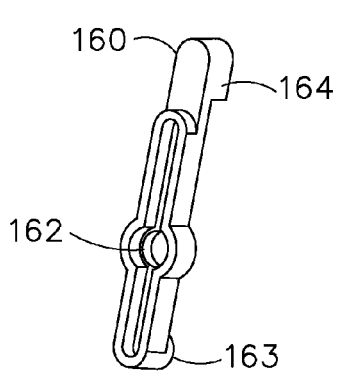
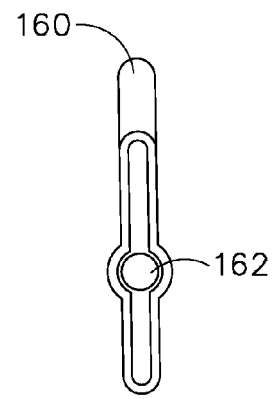
Fig.10          Fig.11
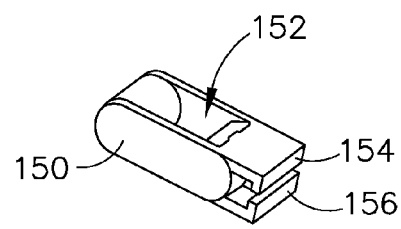
Fig.12
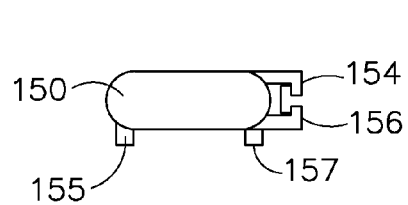     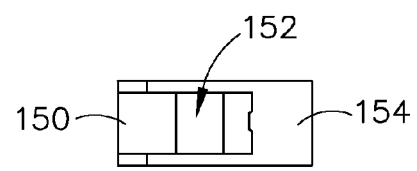
Fig.13          Fig.14

ELECTROSURGICAL INSTRUMENT WITH RESTRICTED TRIGGER

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0083783, entitled "Surgical Instrument with Jaw Member," published Apr. 5, 2012, issued as U.S. Pat. No. 8,888,809 on Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, the disclosure of which is incorporated by reference herein; U.S. Pub. No. 2012/0078243, entitled "Control Features for Articulating Surgical Device," published Mar. 29, 2012, issued as U.S. Pat. No. 8,321,058 on Nov. 27, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. Pub. No. 2013/0030428, entitled "Surgical Instrument with Multi-Phase Trigger Bias," published Jan. 31, 2013, issued as U.S. Pat. No. 9,089,327 on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8 depicts a perspective view of a trigger of the handpiece of FIG. 6;

FIG. 9 depicts a side elevational view of the trigger of FIG. 8;

FIG. 10 depicts a perspective view of a pivot arm of the handpiece of FIG. 6;

FIG. 11 depicts a side elevational view of the pivot arm of FIG. 10;

FIG. 12 depicts a perspective view of a translation member of the handpiece of FIG. 6;

FIG. 13 depicts a side elevational view of the translation member of FIG. 12;

FIG. 14 depicts a top plan view of the translation member of FIG. 12;

Figure 1:
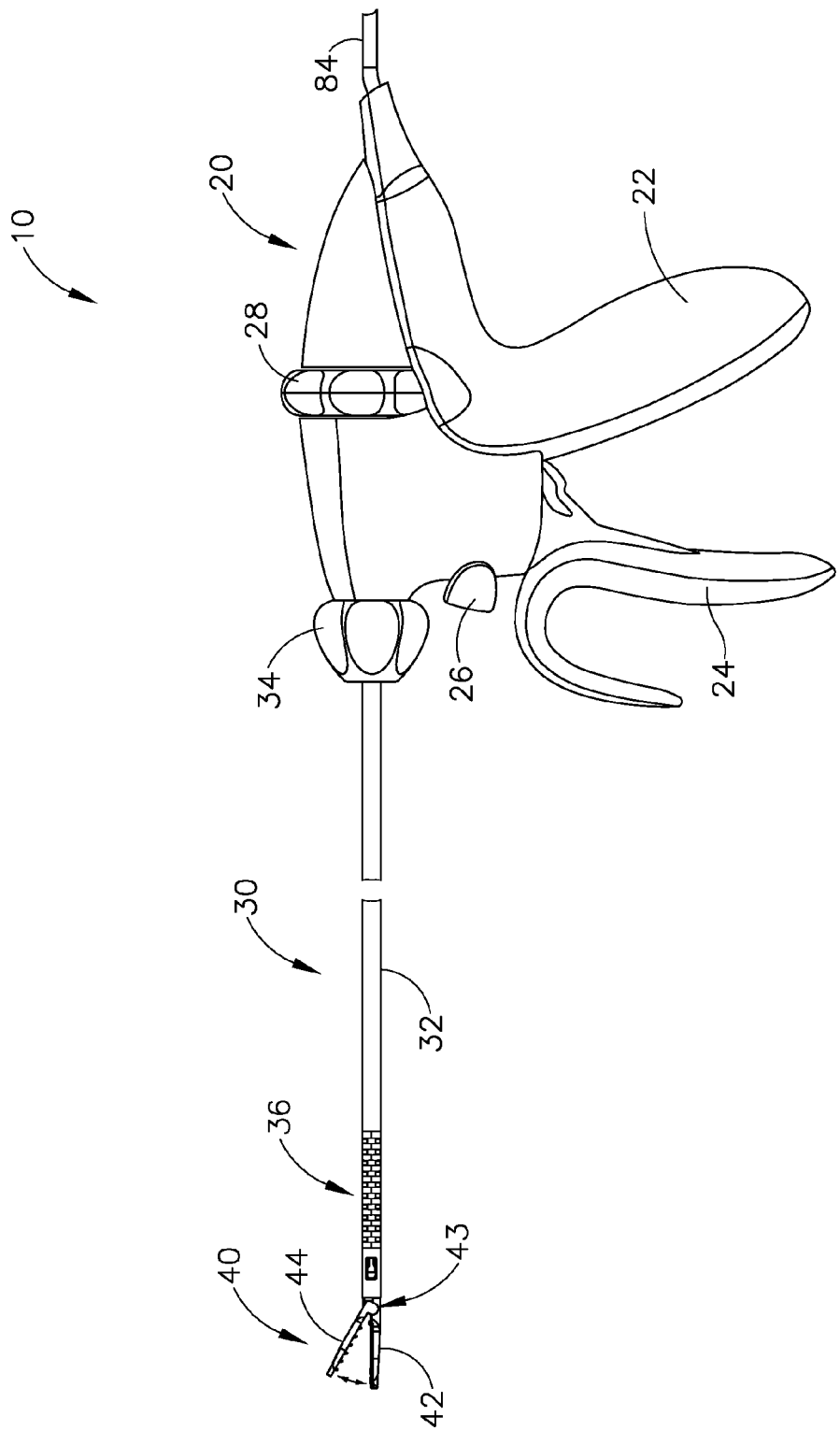
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218 (now U.S. Pat. No. 8,939,974); U.S. Pub. No. 2012/0083783 (now U.S. Pat. No. 8,888,809); U.S. Pub. No. 2012/0116379; U.S. Pub. No. 2012/0078243 (now U.S. Pat. No. 8,321,058); U.S. Pub. No. 2012/0078247; U.S. Pub. No. 2013/0030428 (now U.S. Pat. No. 9,089,327); and/or U.S. Pub. No. 2013/0023868. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively laterally deflect end effector (40) at various angles relative to the longitudinal axis defined by shaft (30). While articulation control (28) is in the form of a rotary dial in the present example, it should be understood that articulation control (28) may take numerous other forms. By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. Pub. No. 2013/0023868, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
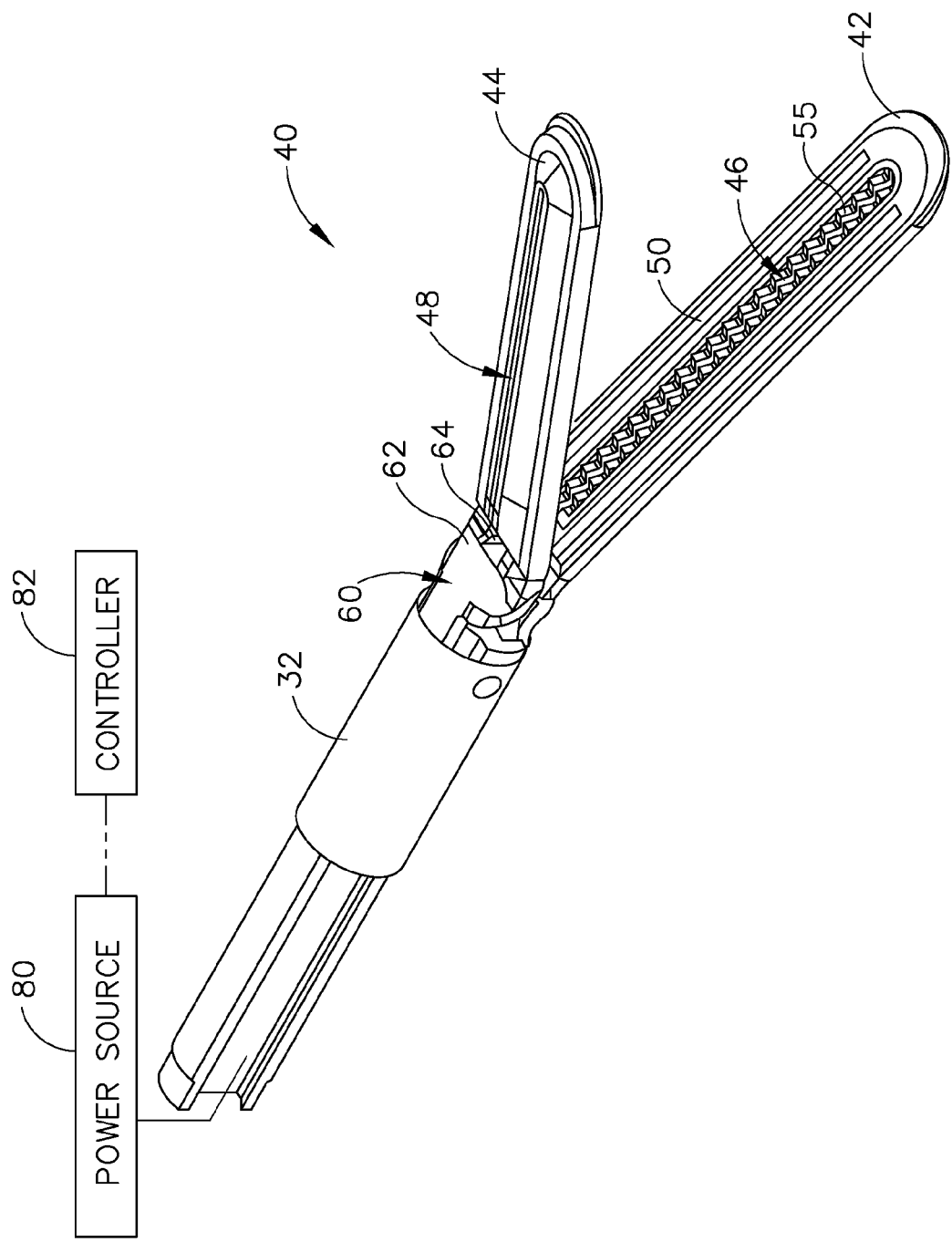
FIG. 2 depicts a perspective view of the end effector of the instrument of FIG. 1, in an open configuration.
Figure 3:
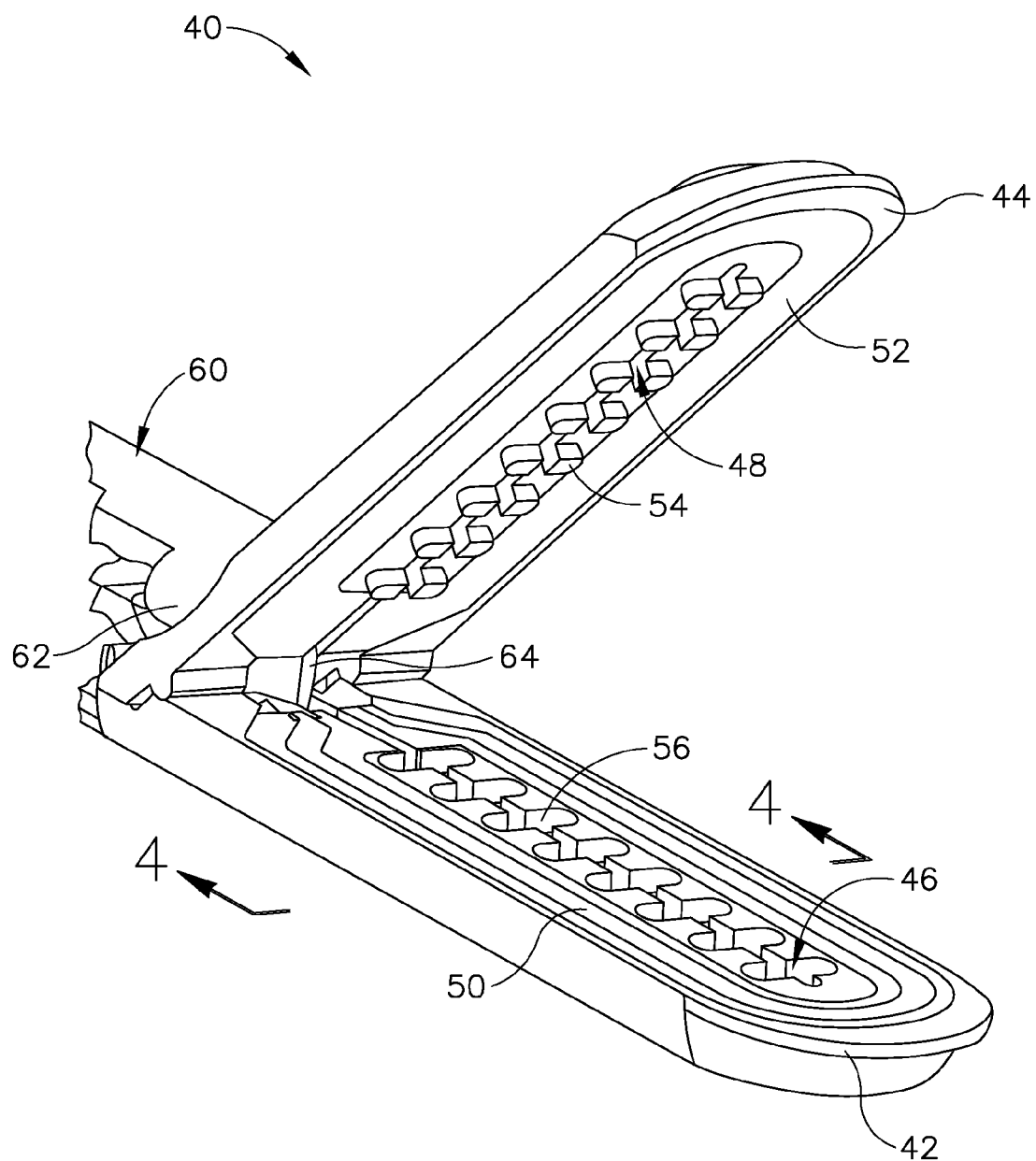
FIG. 3 depicts another perspective view of the end effector of the instrument of FIG. 1, in an open configuration.
Figure 4:
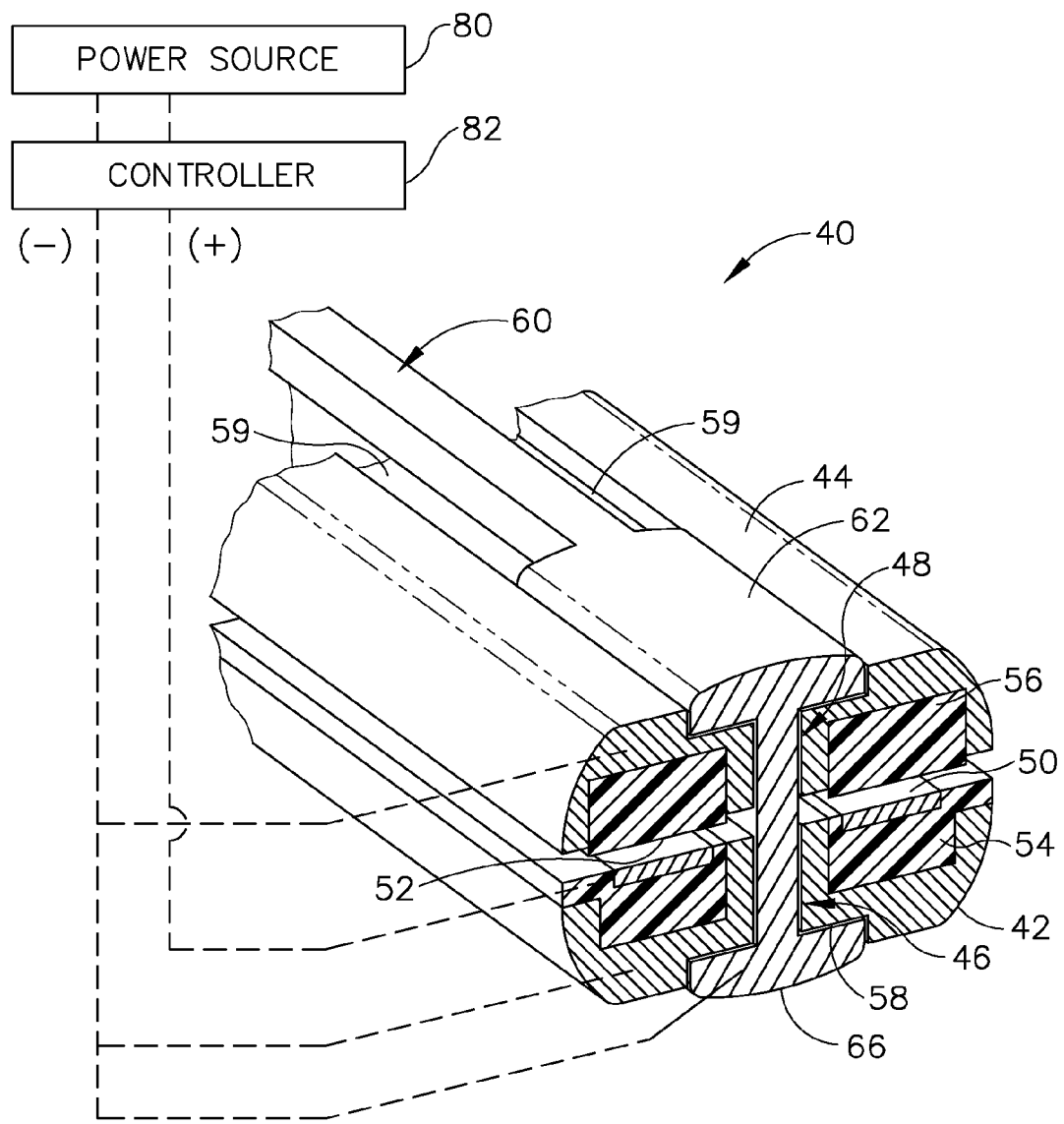
FIG. 4 depicts a cross-sectional end view of the end effector of FIG. 2 taken along line 4-4 of FIG. 3, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768 (expired), entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, issued as U.S. Pat. No. 9,089,360 on Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, issued as U.S. Pat. No. 8,986,202 on Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, issued as U.S. Pat. No. 8,951,248 on Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, issued as U.S. Pat. No. 9,039,695 on May 26, 2015, the disclosure of which is incorporated by reference herein; U.S. Pub. No. 2011/0087215, entitled "Surgical Generator for Ultrasonic and Electrosurgical Devices," published Apr. 14, 2011, issued as U.S. Pat. No. 9,050,993 on Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, issued as U.S. Pat. No. 8,956,349 on Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, issued as U.S. Pat. No. 9,060,776 on Jun. 23, 2015, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. In other words, it should be understood that serrations may be generally blunt or otherwise atraumatic. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw a steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

Figure 5:
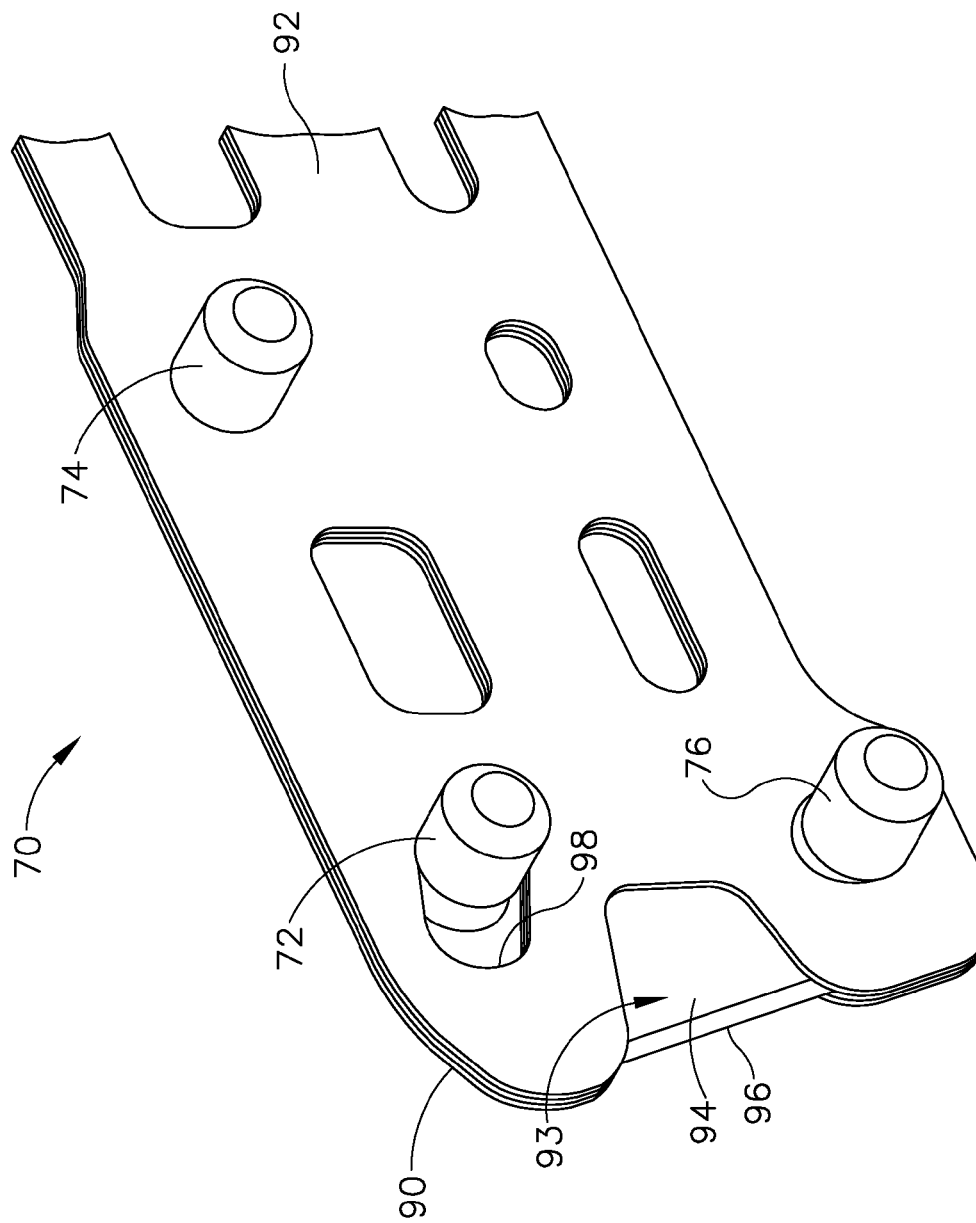
FIG. 5 depicts a partial perspective view of the distal end of an exemplary alternative firing beam suitable for incorporation in the instrument of FIG. 1.

FIG. 5 shows an exemplary alternative firing beam (70), which may be readily substituted for firing beam (60). In this example, firing beam (70) comprises a blade insert (94) that is interposed between two beam plates (90, 92). Blade insert (94) includes a sharp distal edge (96), such that blade insert (94) will readily sever tissue that is captured between jaws (42, 44). Sharp distal edge (96) is exposed by a proximally extending recess (93) formed in plates (90, 92). A set of pins (72, 74, 76) are transversely disposed in plates (90, 92). Pins (72, 74) together effectively serve as substitutes for upper flange (62); while pin (76) effectively serves as a substitute for lower flange (66). Thus, pins (72, 74) bear against channel (59) of jaw (44), and pin (76) bears against channel (58) of jaw (42), as firing beam (70) is translated distally through slots (46, 48). Pins (72, 74, 76) of the present example are further configured to rotate within plates (90, 92), about the axes respectively defined by pins (72, 74, 76). It should be understood that such rotatability of pins (72, 74, 76) may provide reduced friction with jaws (42, 44), thereby reducing the force required to translate firing beam (70) distally and proximally in jaws (42, 44). Pin (72) is disposed in an angled elongate slot (98) formed through plates (90, 92), such that pin (72) is translatable along slot (98). In particular, pin (72) is disposed in the proximal portion of slot (98) as firing beam (70) is being translated distally. When firing beam (70) is translated proximally, pin (72) slides distally and upwardly in slot (98), increasing the vertical separation between pins (72, 76), which in turn reduces the compressive forces applied by jaws (42, 44) and thereby reduces the force required to retract firing beam (70). Of course, firing beam (70) may have any other suitable configuration. By way of example only, firing beam (70) may be configured in accordance with at least some of the teachings of U.S. Pub. No. 2012/0083783 (now U.S. Pat. No. 8,888,809), the disclosure of which is incorporated by reference herein.

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Instrument with Automatic RF Energy

In some instances, it may be desirable to activate electrode surfaces (50, 52) with bipolar RF energy automatically when jaws (42, 44) of end effector (40) are closed. This may prevent inadvertent firing (i.e. distal advancement) of firing beam (14) and cutting edge (48) to sever tissue positioned between jaws (42, 44) without thermally welding the tissue. This may also avoid requiring the operator to actuate a separate user input feature (e.g., like button (26), etc.) to activate RF energy. Accordingly, RF energy features may be provided within instrument (10) to automatically initiate thermal welding of tissue positioned between jaws (42, 44) when jaws (42, 44) are closed. The examples below include several merely illustrative versions of automatic RF energy features that may be readily introduced to an instrument (10).

A. Exemplary Handpiece

Figure 6:
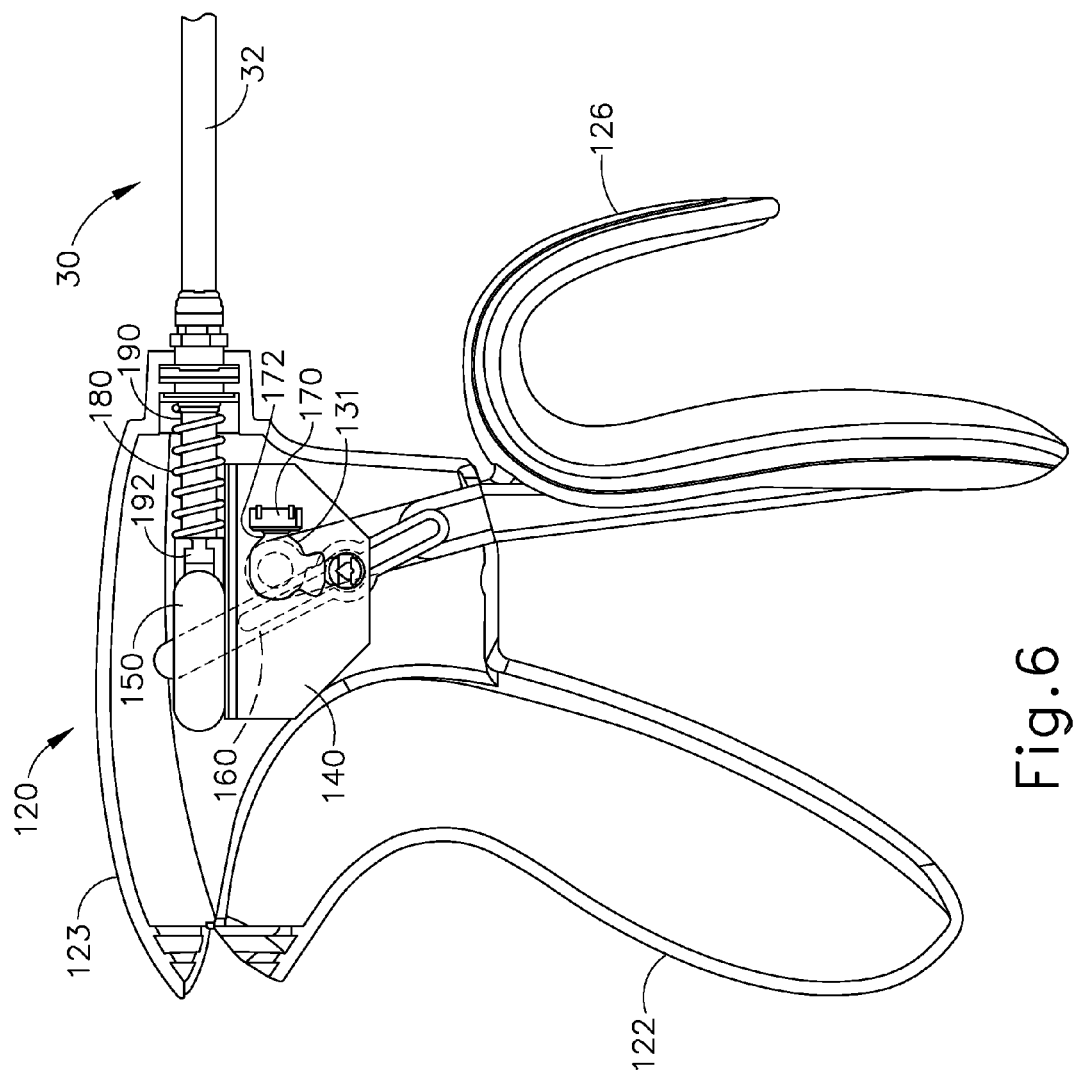
FIG. 6 depicts a cross-sectional view of an exemplary handpiece for use with the instrument of FIG. 1 in an initial position.
Figure 7:
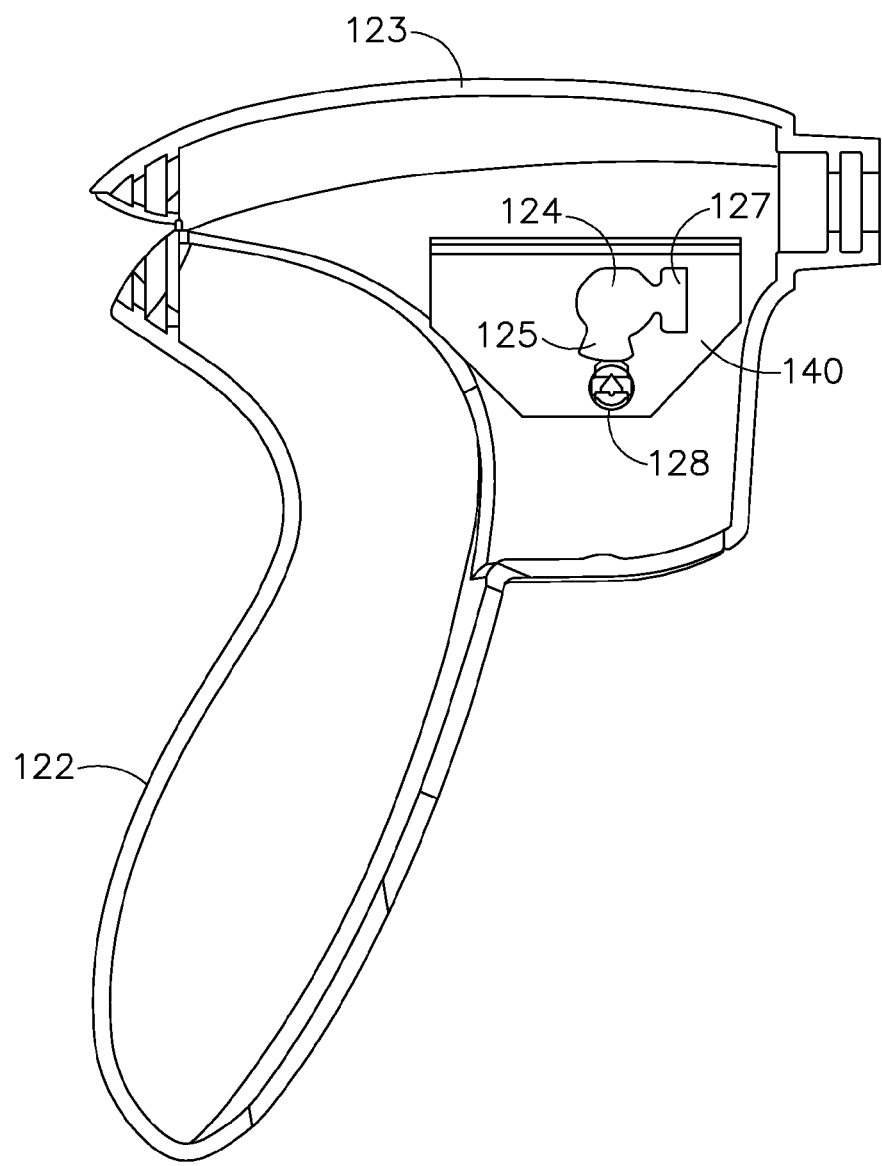
FIG. 7 depicts a cross-sectional view of a housing of the handpiece of FIG. 6.

FIG. 6 shows an exemplary handpiece (120) with automatic RF energy features. Handpiece (120) is similar to handpiece (20) in that handpiece (120) comprises a pistol grip (122) and a trigger (126) that is pivotable toward and away from pistol grip (122) to selectively actuate end effector (40). In the present example, pistol grip (122) is coupled with a housing (123) comprising a plate (140). As shown in FIG. 7, plate (140) comprises a pin (128) and an opening (124). Pin (128) is configured for receipt in an opening (162) of a pivot arm (160). Opening (124) comprises a first recess (125) and a second recess (127). First recess (125) is configured to receive an actuator (131) of trigger (126) such that actuator (131) is rotatable and translatable within first recess (125). In other words, actuator (131) acts as a floating pivot within recess (125). Second recess (127) is configured to receive a switch (170). Switch (170) is operable to selectively activate electrode surfaces (50, 52) of end effector (40) with bipolar RF energy. Accordingly, as actuator (131) of trigger (126) rotates and translates within opening (124), actuator (131) is configured to selectively engage switch (170) to activate and/or deactivate electrode surfaces (50, 52).

FIGS. 8-9 show trigger (126) in greater detail. Trigger (126) comprises an arm (135) extending within housing (123). The top portion of arm (135) comprises an actuator (131) and a protrusion (137). Actuator (131) is substantially circular and is configured to rotate and translate within opening (124) of housing (123). Accordingly, actuator (131) selectively engages switch (170) to activate electrode surfaces (50, 52) with bipolar RF energy. For example, actuator (131) may be in a proximal position such that actuator (131) is decoupled from switch (170) such that no RF energy is supplied to electrode surfaces (50, 52). Trigger (126) may then be pivoted toward grip (122) such that actuator (131) rotates and translates distally within opening (124) to engage and compress switch (170) to apply RF energy to electrode surfaces (50, 52). When trigger (126) is released and pivoted away from grip (122), actuator (131) may return to the proximal position to release switch (170) and again deactivate electrode surfaces (50, 52). A protrusion (133) extends from actuator (131). Protrusion (133) is configured to rotate and translate within first recess (125) opening (124) to prevent actuator (131) from engaging switch (170) prior to closure of jaws (42, 44). The opposing side of the top portion of trigger arm (135) comprises a protrusion (137) extending from arm (135). A pin (136) extends from a side portion of arm (135). The lower portion of arm (135) comprises a channel (138) to receive a protrusion (163) of pivot arm (160).

As shown in FIGS. 10-11, pivot arm (160) comprises opening (162) and protrusions (163, 164). Opening (162) is positioned on pin (128) of plate (140) within housing (123) such that pivot arm (160) is pivotable relative to pin (128). A first protrusion (163) extends from a lower portion of pivot arm (160). First protrusion (163) is configured to extend within channel (138) of trigger arm (135). Accordingly, a user may pivot trigger (126) toward and/or away from grip (122) to thereby pivot arm (160) with trigger (126). A second protrusion (164) extends from a top portion of pivot arm (160) to extend within translation member (150). Translation member (150) thereby translates upon rotation of pivot arm (160).

Translation member (150) comprises a channel (152) extending through translation member (150) to receive second protrusion (164) of pivot arm (160), as shown in FIGS. 12-14. Translation member (150) further comprises arms (154, 156) extending distally from translation member (150), as best seen in FIG. 13. First arm (154) extends outwardly and downwardly from a top portion of the distal end of translation member (150). Second arm (156) extends outwardly and upwardly from a lower portion of the distal end of translation member (150). Arms (154, 156) may therefore receive the proximal end of firing beam (190), as shown in FIG. 6. Firing beam (190) is substantially similar to firing beam (60), except that the proximal end of firing beam (190) comprises a knob (192). Knob (192) is positioned within arms (154, 156) of translation member (150) to maintain the longitudinal position of firing beam (190) relative to translation member (150). Accordingly, translation member (150) is operable to translate firing beam (190). A compression spring (180) is positioned around firing beam (190) distal to arms (154, 156) of translation member (150). Compression spring (180) is configured to resiliently bias translation member (150) proximally to an initial position such that jaws (42, 44) are open. Pins (155, 157) extend from a bottom surface of translation member (150), as shown in FIG. 13. Pins (155, 157) engage plate (140) of housing (123) such that translation member (150) is translatable proximally and/or distally relative to plate (140).

Figure 15:
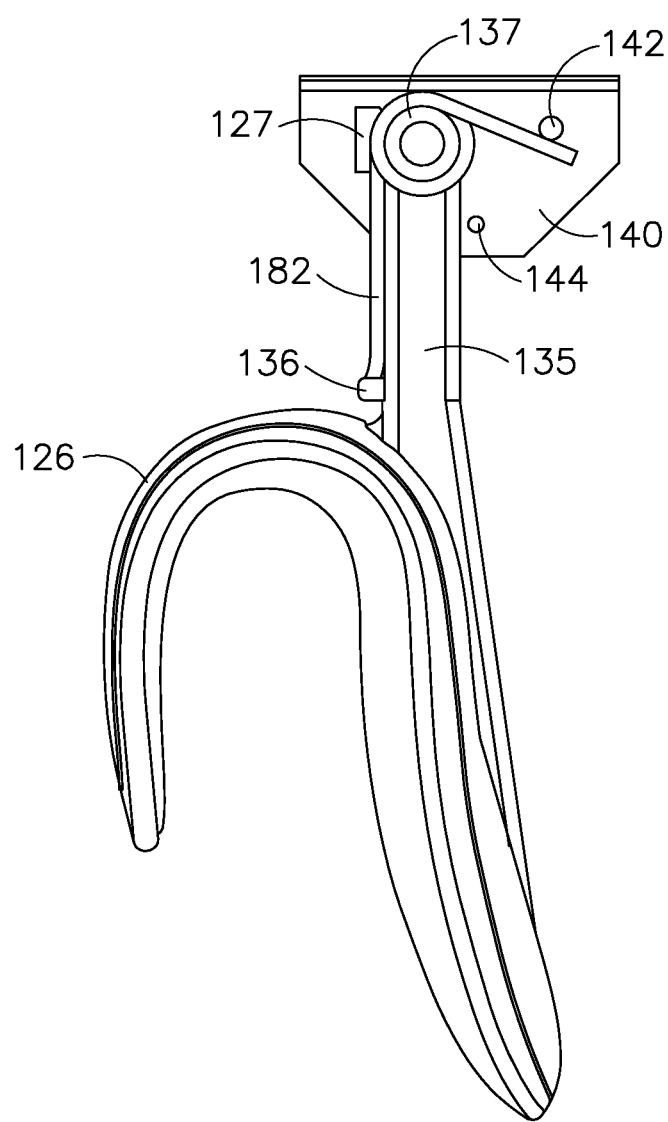
FIG. 15 depicts a side elevational view of the trigger coupled to a plate of the handpiece of FIG. 6.

In the present example, a torsion spring (182) is further provided to resiliently bias trigger (126) to the initial position such that jaws (42, 44) are open, as shown in FIG. 15. Torsion spring (182) is positioned around protrusion (137) of trigger arm (135). One end of torsion spring (182) rests against pin (136) on the side portion of trigger arm (135). The opposing end of torsion spring (182) rests against a pin (142) extending from plate (140). Accordingly, as trigger (126) is pivoted toward grip (122), torsion spring (182) is compressed to resiliently bias trigger (126) back to the initial position away from grip (122). Plate (140) comprises a detent (144) positioned proximal to trigger arm (135) when trigger (126) is in the initial position. When trigger (126) is pivoted proximally toward grip (122), trigger arm (135) passes detent (144) such that detent (144) is operable to provide a tactile (and perhaps audible) warning. Detent (144) is positioned such that the tactile warning is provided just prior to actuator (131) compressing switch (170) to activate the bipolar RF energy. However, detent (144) is merely optional and other warning methods (e.g., audible, visual, etc.) may be used to indicate the activation of bipolar RF energy. Other suitable warning features and methods will be apparent to one with ordinary skill in the art in view of the teachings herein.

B. Exemplary Operation

Figure 16A:
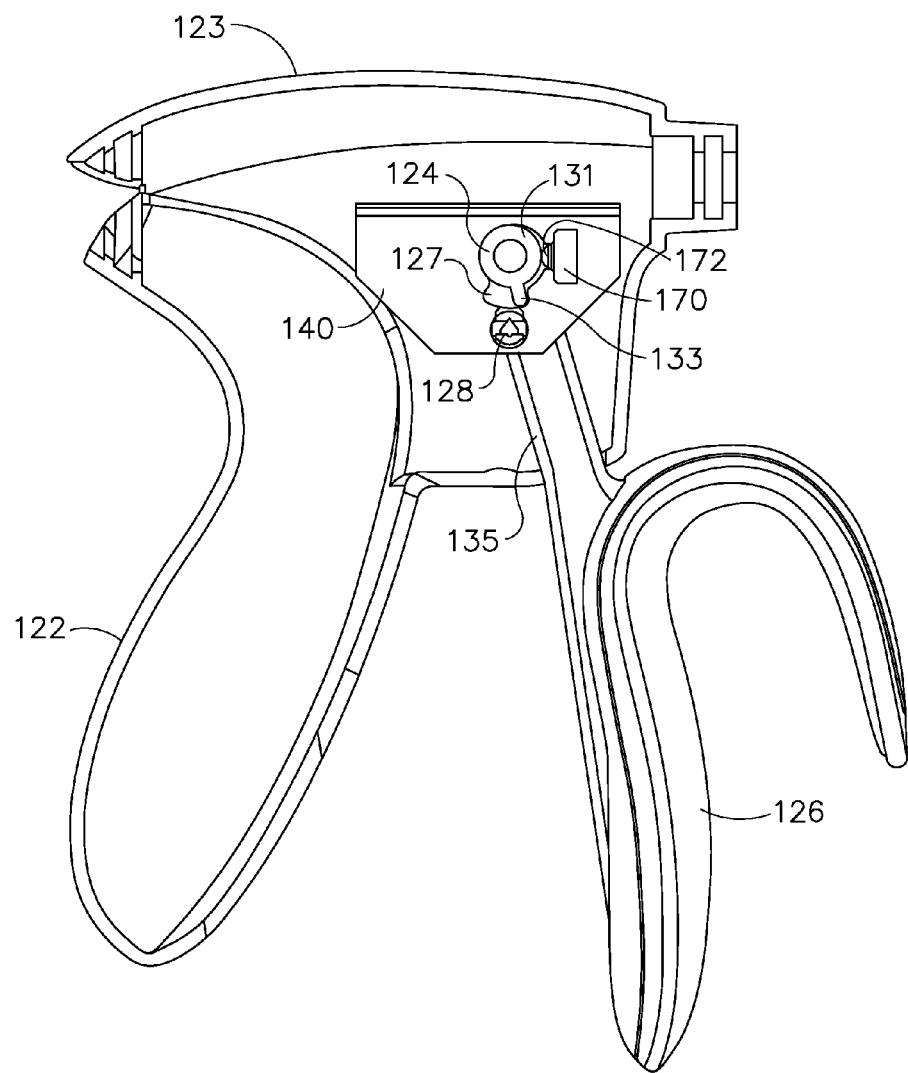
FIG. 16A depicts a partial cross-sectional view of the handpiece of FIG. 6 in the initial position.

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Once end effector (40) is positioned within the patient, jaws (42, 44) are opened. Trigger (126) is then at an initial position, as shown in FIG. 16A, such that trigger (126) is pivoted away from grip (122). In this position, actuator (131) is at a proximal position such that actuator (131) is decoupled from switch (170). As shown in FIG. 6, translation member (150) is also in a proximal position such that firing beam (190) is proximal and jaws (42, 44) of end effector (40) are open.

Figure 17:
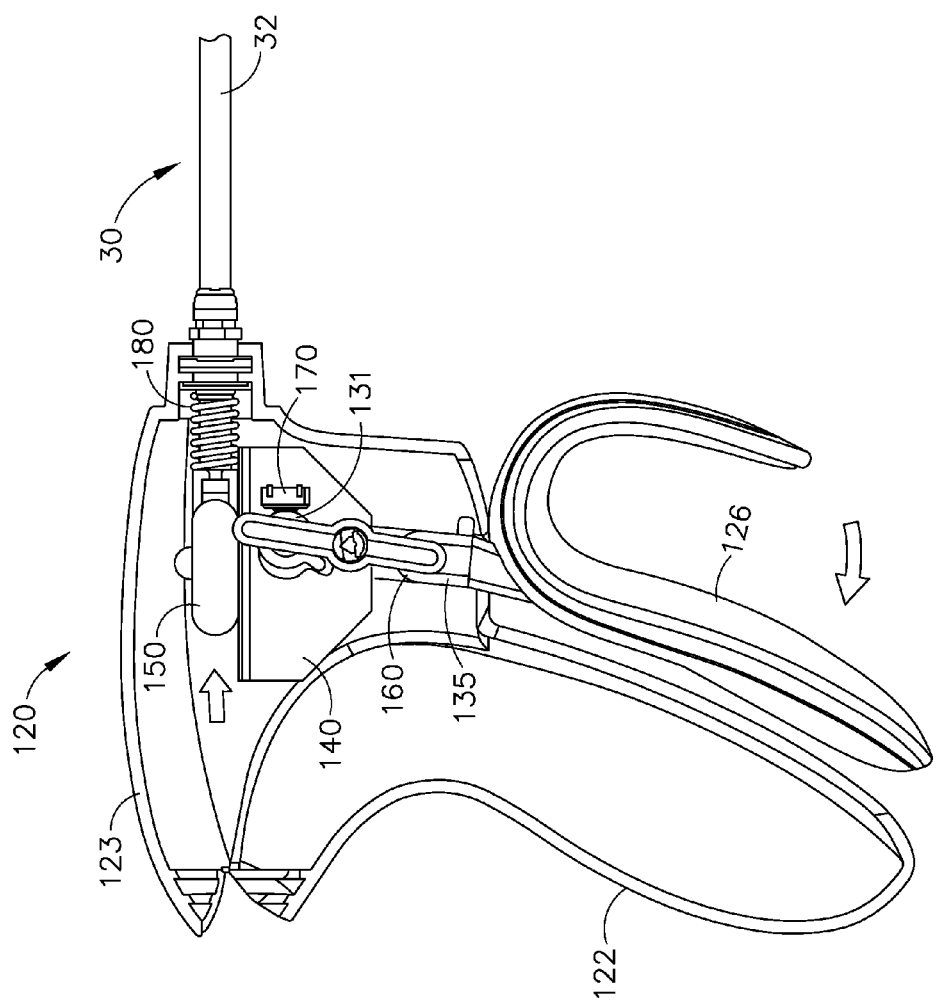
FIG. 17 depicts a cross-sectional view of the handpiece of FIG. 6 in the fired position.

Two layers of tissue of the anatomical structure are then captured between jaws (42, 44) by squeezing trigger (126) toward pistol grip (122) through a first range of motion. When trigger (126) is pivoted toward grip (122) through this first range of motion, protrusion (163) of pivot arm (160) translates with trigger arm (135) within channel (138). Pivot arm (160) thereby pivots around pin (128) of plate (140) such that the top portion of pivot arm (160) moves distally. Accordingly, protrusion (164) of pivot arm (160) translates translation member (150) and firing beam (190) distally, as shown in FIG. 17. As noted above, flanges (62, 66) cammingly act to pivot jaw (42) toward jaw (44) when firing beam (190) is actuated distally by squeezing trigger (126) toward pistol grip (122). Jaws (42, 44) may be substantially clamping tissue before trigger (122) has swept through a full range of motion toward pistol grip (122), such that trigger (126) may continue pivoting toward pistol grip (122) through a second range of motion after jaws (42, 44) have substantially clamped on the tissue. Detent (144) provides tactile feedback to the operator indicating that trigger (126) has completed the first range of motion.

It should be understood that protrusion (133) sweeps through first recess (125) during a first range of pivotal motion of trigger (126) as described above, and that actuator (131) remains decoupled from switch (170) during this range of motion. Thus, electrodes (50, 52) remain inactive as trigger (126) pivots through the first range of motion. This ensures that electrodes (50, 52) do not receive RF energy before tissue is clamped between jaws (42, 44). Once trigger (126) completes the first range of motion and has advanced firing beam (190) to the point where tissue is clamped between jaws (42, 44), protrusion (133) reaches the proximal end of recess (125) such that further pivoting of trigger (126) through a second range of motion will drive actuator (131) distally in opening (124), to thereby active switch (170).

Figure 16B:
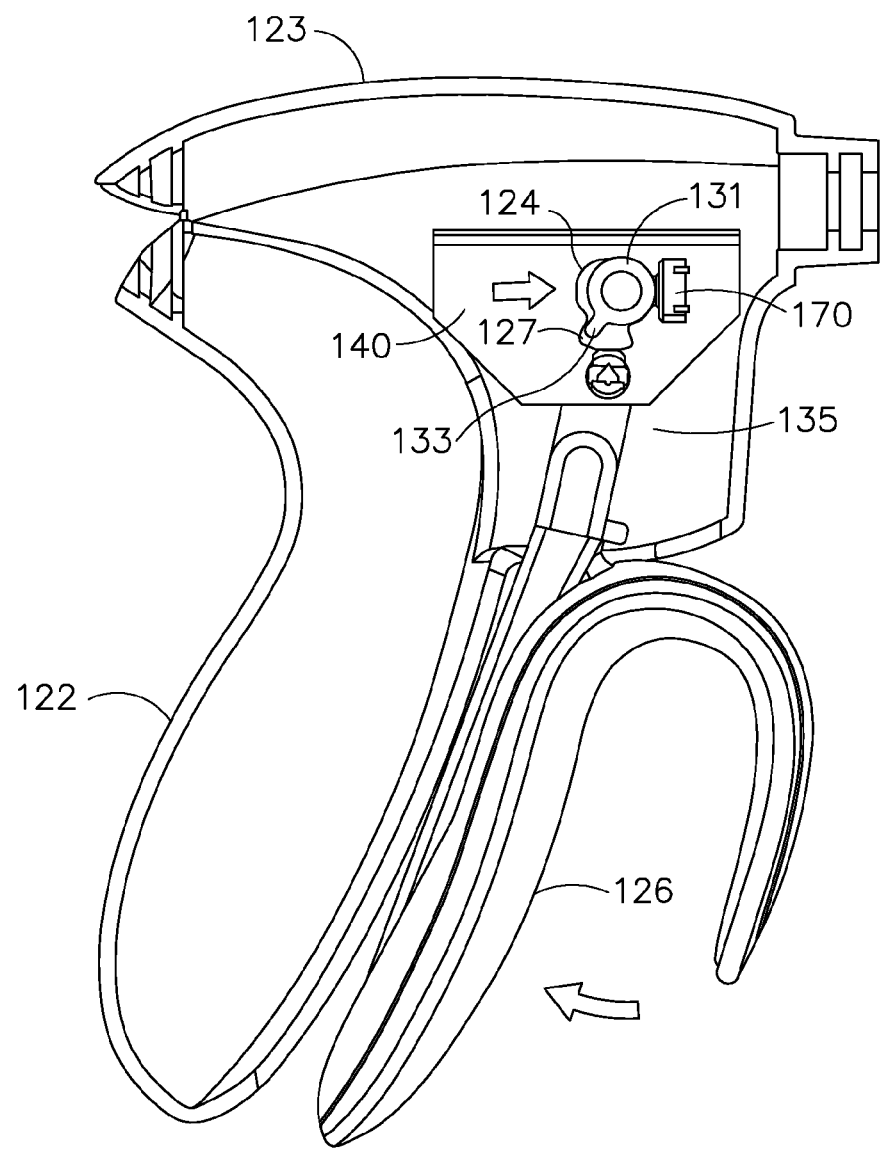
FIG. 16B depicts a partial cross-sectional view of the handpiece of FIG. 6 in a fired position.

With tissue layers clamped between jaws (42, 44), firing beam (190) continues to advance distally by the user squeezing trigger (126) further toward pistol grip (122) through a second range of motion. This further pivoting of trigger (126) through the second range of motion activates switch (170), as shown in FIG. 16B, to deliver bipolar RF energy to electrodes (50, 52). In some versions, electrodes (50, 52) are selectively coupled with power source (80) (e.g., by depressing switch (170), etc.) such that electrode surfaces (50, 52) of jaws (42, 44) are activated with a common first polarity while firing beam (190) is activated at a second polarity that is opposite to the first polarity. Thus, a bipolar RF current flows between firing beam (190) and electrode surfaces (50, 52) of jaws (42, 44), through the compressed regions of severed tissue layer portions. In some other versions, electrode surface (50) has one polarity while electrode surface (52) and firing beam (190) both have the other polarity. In either version (among at least some others), bipolar RF energy delivered by power source (80) ultimately thermally welds the tissue layer portions on one side of firing beam (190) together and the tissue layer portions on the other side of firing beam (190) together.

The further pivoting of trigger (126) through the second range of motion also causes firing beam (190) to continue advancing distally. As firing beam (190) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44).

End effector (40) may then be removed from the patient or repositioned to sever additional tissue. If end effector (40) is repositioned, trigger (126) may be released to open jaws (42, 44). Torsion spring (182) biases trigger (126) to the initial position and compression spring (180) biases translation member (150) proximally to the initial position, shown in FIGS. 6 and 16A. Accordingly, actuator (131) is translated proximally within opening (124) to release switch (170), as shown in FIG. 16A, to thereby deactivate the RF energy. The proximal translation of translation member (150) pulls firing beam (190) proximally to open jaws (42, 44) of end effector (40). Accordingly, end effector (40) may then be repositioned to sever additional tissue.

Figure 18:
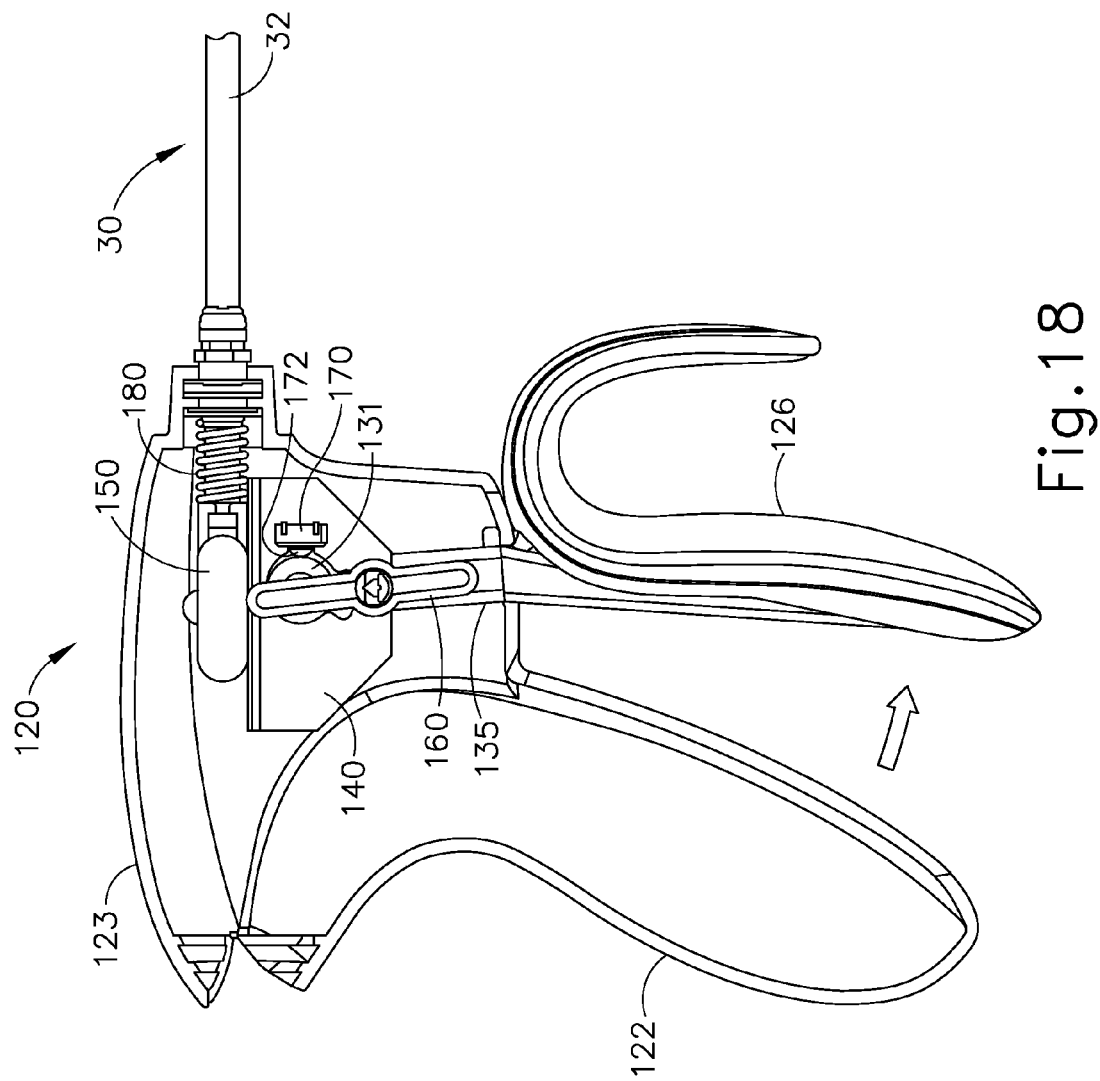
FIG. 18 depicts a cross-sectional view of the handpiece of FIG. 6 in a fired and de-energized state.

In some instances, it may be desirable to deactivate the RF energy without opening jaws (42, 44) of end effector (40). After pivoting trigger (126) toward grip (122) to activate the RF energy, the user may slightly release trigger (126) to the position shown in FIG. 18. Trigger (126) is pivoted slightly away from grip (122) such that torsion spring (182) biases actuator (131) of trigger arm (135) proximally within opening (124) to release switch (170). The decompression of switch (170) thereby deactivates the RF energy. Because trigger (126) was slightly released from grip (122), translation member (150) remains at a distal position such that firing beam (190) is still sufficiently advanced to clamp jaws (42, 44) together. Accordingly, the RF energy has been deactivated from end effector (40) with jaws (42, 44) still closed.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603 (expired), filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193 (now U.S. Pat. No. 8,408,439), entitled "Surgical Stapling Instrument with An Articulatable End Effector," published Oct. 21, 2010; issued as U.S. Pat. No. 8,408,439 on Apr. 2, 2013; and U.S. Pub. No. 2012/0239012 (now U.S. Pat. No. 8,453,914), entitled "Motor-Driven Surgical Cutting Instrument with Electric Actuator Directional Control Assembly," published Sep. 20, 2012, issued as U.S. Pat. No. 8,453,914 on Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874 (abandoned), entitled "Tissue Pad for Use with an Ultrasonic Surgical Instrument," published Apr. 13, 2006, the disclosure of which is incorporated by reference herein; U.S. Pat. Pub. No. 2007/0191713 (abandoned), entitled "Ultrasonic Device for Cutting and Coagulating," published Aug. 16, 2007, the disclosure of which is incorporated by reference herein; U.S. Pat. Pub. No. 2007/0282333 (abandoned), entitled "Ultrasonic Waveguide and Blade," published Dec. 6, 2007, the disclosure of which is incorporated by reference herein; U.S. Pat. Pub. No. 2008/0200940 (abandoned), entitled "Ultrasonic Device for Cutting and Coagulating," published Aug. 21, 2008, the disclosure of which is incorporated by reference herein; U.S. Pat. Pub. No. 2011/0015660 (now U.S. Pat. No. 8,461,744), entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) an end effector, wherein the end effector comprises:
      (i) a first jaw,
      (ii) a second jaw, wherein the first jaw is pivotable relative to the second jaw, wherein the first jaw is configured to pivot from an open position to a closed position, wherein one or both of the first jaw or the second jaw is operable to deliver energy to tissue, and
      (iii) a cutting member operable to sever tissue captured between the first and second jaws;
   (b) a first actuator, wherein the first actuator is movable from a first position to a second position, wherein the first actuator is operable to pivot the first jaw from the open position to the closed position when the first actuator is moved from the first position to the second position, wherein the first actuator is further operable to drive the cutting member when the first actuator is moved from the second position to a third position; and
   (c) a second actuator, wherein the first actuator is configured to engage the second actuator when the first actuator is in the second position, wherein the second actuator is operable to selectively energize the one or both of the first jaw or the second jaw to deliver energy to tissue when the first actuator is engaged with the second actuator.

2. The apparatus of claim 1 further comprising a handpiece, wherein the first and second actuators are positioned within the handpiece.

3. The apparatus of claim 2, wherein the first actuator is movable within an opening of the handpiece.

4. The apparatus of claim 2, wherein the second actuator comprises a switch.

5. The apparatus of claim 4, wherein the switch is positioned within an opening of the handpiece.

6. The apparatus of claim 2, wherein the handpiece comprises a trigger pivotable relative to the handpiece, wherein the first actuator is positioned on a top portion of the trigger.

7. The apparatus of claim 6 further comprising a pivot arm, wherein the pivot arm is pivotable relative to the handpiece, wherein the pivot arm is coupled with the trigger such that the trigger is operable to pivot the pivot arm relative to the handpiece.

8. The apparatus of claim 7 further comprising a translation member, wherein the translation member is coupled with the pivot arm such that the pivot arm is operable to translate the translation member relative to the handpiece.

9. The apparatus of claim 8 further comprising a firing beam, wherein the firing beam is coupled with a distal end of the translation member, wherein the translation member is operable to translate the firing beam.

10. The apparatus of claim 9, wherein the cutting member is positioned at the distal end of the firing beam.

11. The apparatus of claim 8, further comprising a resilient member coupled with the translation member such that the resilient member is operable to bias the translation member to a proximal position.

12. The apparatus of claim 2, wherein the handpiece comprises an indicator operable to indicate that the first actuator is moving from the first position to the second position.

13. The apparatus of claim 12, wherein the indicator is a detent positioned within the handpiece.

14. The apparatus of claim 1, wherein the first actuator comprises a protrusion, wherein the protrusion is operable to prevent the first actuator from engaging the second actuator prior to the first jaw pivoting to the closed position.

15. The apparatus of claim 1, wherein the first actuator is configured to disengage the second actuator while the first jaw is in the closed position.

16. The apparatus of claim 1, wherein the one or both of the first jaw or the second jaw is operable to deliver RF energy to tissue, wherein the second actuator is operable to selectively energize the one or both of the first jaw or the second jaw to deliver RF energy to tissue when the first actuator is engaged with the second actuator.

17. An apparatus for operating on tissue, the apparatus comprising:
   (a) an end effector, wherein the end effector comprises a first jaw and a second jaw, wherein the first jaw is pivotable relative to the second jaw, wherein the first jaw is configured to pivot from an open position to a closed position;
   (b) a first actuator, wherein the first actuator is pivotable from a first position to a second position;
   (c) a second actuator coupled with the first actuator, wherein the second actuator is translatable from a proximal position to a distal position when the first actuator is pivoted from the first position to the second position, wherein the second actuator is operable to pivot the first jaw from the open position to the closed position when the second actuator is translated from the proximal position to the distal position; and
   (d) a third actuator, wherein the first actuator is configured to actuate the third actuator when the first actuator moves from the first position to the second position, wherein the third actuator is operable to selectively provide RF energy to the end effector.

18. A method of operating an apparatus, the apparatus comprising an end effector having a first and second jaw, a first actuator, and a second actuator, the method comprising:
   (a) positioning the first and second jaws of the end effector around tissue;
   (b) actuating the first actuator through a first range of motion to pivot the first jaw toward the second jaw to clamp the tissue between the first and second jaws; and
   (c) actuating the first actuator through a second range of motion to actuate the second actuator, wherein the second actuator provides RF energy to the end effector to weld the tissue.

19. The method of claim 18, further comprising actuating the first actuator through a third range of motion to sever the tissue clamped between the first and second jaws of the end effector.

20. The method of claim 18, further comprising reversing the first actuator to de-actuate the second actuator such that the second actuator deactivates the RF energy to the end effector while the first jaw remains pivoted toward the second jaw.

* * * * *